United States Patent
van der Leest (10) Patent No.: US 9,566,177 B2
(45) Date of Patent: Feb. 14, 2017

(54) BIORESORBABLE VASCULAR IMPLANT HAVING HOMOGENOUSLY DISTRIBUTED STRESSES UNDER A RADIAL LOAD

(75) Inventor: Machiel van der Leest, Paris (FR)

(73) Assignee: Artertial Remodeling Technologies, S.A. (FR)

( * ) Notice: Subject to any disclaimer, the term of this patent is extended or adjusted under 35 U.S.C. 154(b) by 577 days.

(21) Appl. No.: 12/899,425

(22) Filed: Oct. 6, 2010

(65) Prior Publication Data
US 2011/0112626 A1    May 12, 2011

Related U.S. Application Data

(60) Provisional application No. 61/249,010, filed on Oct. 6, 2009.

(51) Int. Cl.
 *A61F 2/82* (2013.01)
 *A61F 2/915* (2013.01)
 *A61F 2/91* (2013.01)

(52) U.S. Cl.
 CPC ............... *A61F 2/915* (2013.01); *A61F 2/91* (2013.01); *A61F 2210/0004* (2013.01)

(58) Field of Classification Search
 CPC ........................................................ A61F 2/82
 USPC ....................................................... 623/1.15
 See application file for complete search history.

(56) References Cited

U.S. PATENT DOCUMENTS

| 619,406 A1 | 2/2001 | Duering et al. |
|---|---|---|
| 6,540,774 B1 | 4/2003 | Cox |
| 7,753,948 B2 | 7/2010 | Roeder et al. |
| 2002/0058988 A1 | 5/2002 | Fischell et al. |
| 2003/0216804 A1 | 11/2003 | DeBeer et al. |
| 2004/0249442 A1 | 12/2004 | Fleming, III et al. |
| 2006/0058863 A1 | 3/2006 | LaFont et al. |
| 2006/0271170 A1 | 11/2006 | Gale et al. |
| 2007/0021824 A1 | 1/2007 | Roeder et al. |
| 2007/0203569 A1 | 8/2007 | Burgermeister et al. |
| 2008/0065195 A1 | 3/2008 | Brown et al. |
| 2008/0275537 A1 | 11/2008 | Limon |

(Continued)

FOREIGN PATENT DOCUMENTS

| JP | 2005334632 | 12/2005 |
|---|---|---|
| JP | 2006334171 | 12/2006 |

(Continued)

OTHER PUBLICATIONS

An International Search Report dated Mar. 28, 2011, 4 pgs.

*Primary Examiner* — Matthew Schall
(74) *Attorney, Agent, or Firm* — Tarolli, Sundheim, Covell & Tummino LLP (57) ABSTRACT

A bioresorbable vascular implant for implantation in a bodily lumen has a tubular framework and includes one or more annular support members. Each of the one or more annular support members includes a plurality of struts interconnected by a hinge region. Each of the plurality of struts also includes a mid-section. The vascular implant also includes at least one viscoelastic material that enables transition of the vascular implant between a collapsed configuration and an expanded configuration. Each of the plurality of struts and the hinge region defines a cross-section. The moment of inertia increases from the mid-section towards the hinge region to accommodate the transition and resist a radial load applied to the vascular implant in the expanded configuration.

15 Claims, 9 Drawing Sheets

(56) References Cited

U.S. PATENT DOCUMENTS

| | | |
|---|---|---|
| 2008/0319540 A1 | 12/2008 | Jordan et al. |
| 2010/0004728 A1* | 1/2010 | Rao .......................... A61F 2/07 |
| | | 623/1.11 |

FOREIGN PATENT DOCUMENTS

| | | |
|---|---|---|
| JP | 2007314797 | 12/2007 |
| WO | 9942147 | 8/1999 |
| WO | WO-99/65418 A1 | 12/1999 |
| WO | 0167990 | 9/2001 |
| WO | WO-2005/096992 A1 | 10/2005 |
| WO | WO-2007/105067 A1 | 9/2007 |
| WO | 2009103011 | 8/2009 |

* cited by examiner

BIORESORBABLE VASCULAR IMPLANT HAVING HOMOGENOUSLY DISTRIBUTED STRESSES UNDER A RADIAL LOAD

RELATED APPLICATION

This application claims priority from U.S. Provisional Patent Application Ser. No. 61/249,010, filed on Oct. 6, 2009, the subject matter of which is incorporated herein by reference.

TECHNICAL FIELD

The present invention relates generally to an implantable vascular device for interventional therapeutic treatment or vascular surgery, and more particularly to a bioresorbable polymeric scaffold that exhibits a homogeneous stress distribution in both collapsed and expanded configurations.

BACKGROUND OF THE INVENTION

The art and science of interventional therapy and surgery has continually progressed towards treatment of internal defects and diseases by use of ever smaller incisions or access through the vasculature or bodily openings to reduce tissue trauma surrounding the treatment site. One important aspect of such treatments involves percutaneous placement of stents or scaffolds at a given treatment site (or sites).

Stents are typically introduced within a vessel in a collapsed configuration and then expanded when placed in the vessel to maintain patency of the vessel. Stent expansion is either memory-based (i.e., self-expanding), deformation-based (i.e., balloon expanding), or a combination of both. Stents that are expanded using deformation-based techniques include areas of concentrated stresses in predetermined areas to control the deformation. For example, balloon-expandable stents have high stress areas in the hinges to facilitate controlled crimping and subsequent expansion.

As a result of this construction, however, when applied, the stresses are the highest in these areas, such as in the expanded state under radial load from the vessel or bodily openings. In the case of polymeric stents or scaffolds, these concentrated stress areas can be subject to deformation due to the viscoelastic properties of the polymer material, thus leading to undesirable and deleterious effects to the stent (i.e., stent collapse or recoil).

SUMMARY OF THE INVENTION

According to one aspect of the present invention, a bioresorbable vascular implant for implantation in a bodily lumen has a tubular framework comprising one or more annular support members. Each of the one or more annular support members includes a plurality of struts interconnected by a hinge region. Each of the plurality of struts also includes a mid-section. The vascular implant is comprised of at least one viscoelastic material that enables transition of the vascular implant between a collapsed configuration and an expanded configuration. Each of the plurality of struts and the hinge region defines a cross-section. The moment of inertia increases from the mid-section towards the hinge region to accommodate the transition and resist a radial load applied to the vascular implant in the expanded configuration.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6 is a stress vs. strain curve for the vascular implant in FIGS. 1A-B from which maximum stresses and yield stresses can be read. Stents were submerged in water at 37° C. and radially compressed after 2 minutes in three consecutive cycles with a radial tester RCM-60-WB from MPT Europe (Mulderspark 9-1, 9351 NR Leek, the Netherlands). During the first cycle (Curve A), a 15% diameter reduction was applied. During the second cycle (Curve B), an additional 15% diameter reduction was applied. During the second cycle (Curve C), the stent diameter was reduced to 1.7 mm. As can be seen, the stent returned to its initial diameter after the first cycle and, after the second cycle, the stent plastically deformed;

DETAILED DESCRIPTION

Unless otherwise defined, all technical terms used herein have the same meaning as commonly understood by one of ordinary skill in the art to which the present invention pertains.

In the context of the present invention, the term "subject" can refer to any warm-blooded organism including, but not limited to, human beings, pigs, rats, mice, dogs, goats, sheep, horses, monkeys, apes, rabbits, cattle, etc.

As used herein, the term "bioresorbable polymer" can refer to a polymer whose degradation by-products can be bio-assimilated or excreted via natural pathways in a subject's body.

As used herein, the term "crimping" can refer to a process that involves radial pressing on a vascular implant to allow a decrease in the diameter of the vascular implant without substantially affecting the structural components of the vascular implant (e.g., the wall or struts).

As used herein, the term "degradable polymer" can refer to a polymer that breaks down into monomers and oligomers when placed in a subject's body or in an aqueous solution and maintained under conditions of temperature, osmolality, pH, etc., that mimic physiological media, preferably without involving enzymatic degradation to minimize the risk of triggering the antigen-antibody defense system of the subject.

As used herein, the term "final predetermined shape and diameter" can refer to the desired diameter, length, design, and wall thickness of a vascular implant that has been deployed into a bodily lumen.

As used herein, the term "negative recoil" can refer to an undesirable decrease in the diameter of an expanded vascular implant.

As used herein, the term "positive recoil" can refer to an increase in the diameter of a vascular implant that has been educated to have a desired final diameter but has not been fully expanded to the desired final diameter.

As used herein, the terms "glass transition temperature" and "Tg" can refer to the temperature at which a polymer changes from a glassy state to a rubbery state and vice-versa.

As used herein, the term "relaxation-related recoil" can refer to the slow change in dimensions of a vascular implant due to a time-dependent slow rearrangement of molecule conformations according to a well known behavior of viscoelastic polymeric materials. Such rearrangement is partly due to a permanent static or dynamic load that slowly leads the polymeric material comprising a vascular implant to a thermodynamic equilibrium.

Figure 1A:
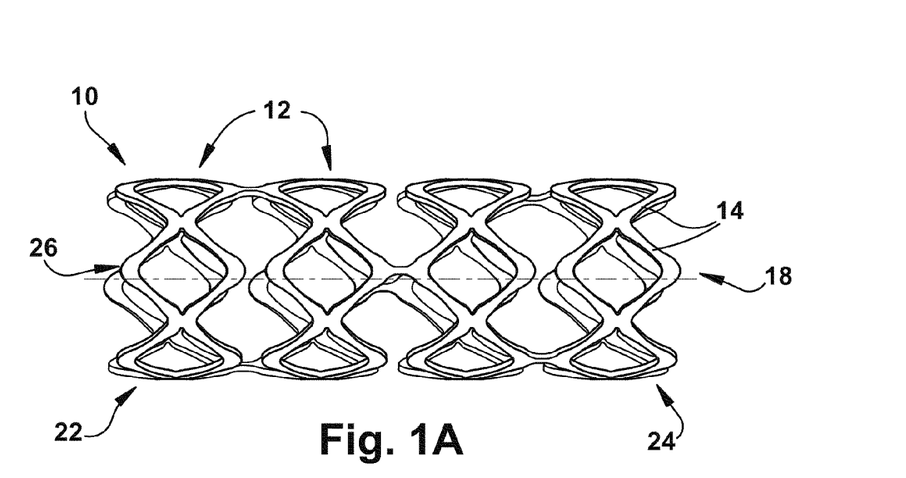
FIG. 1A is a schematic illustration showing a bioresorbable vascular implant in an expanded configuration and constructed in accordance with one aspect of the present invention.
Figure 1B:
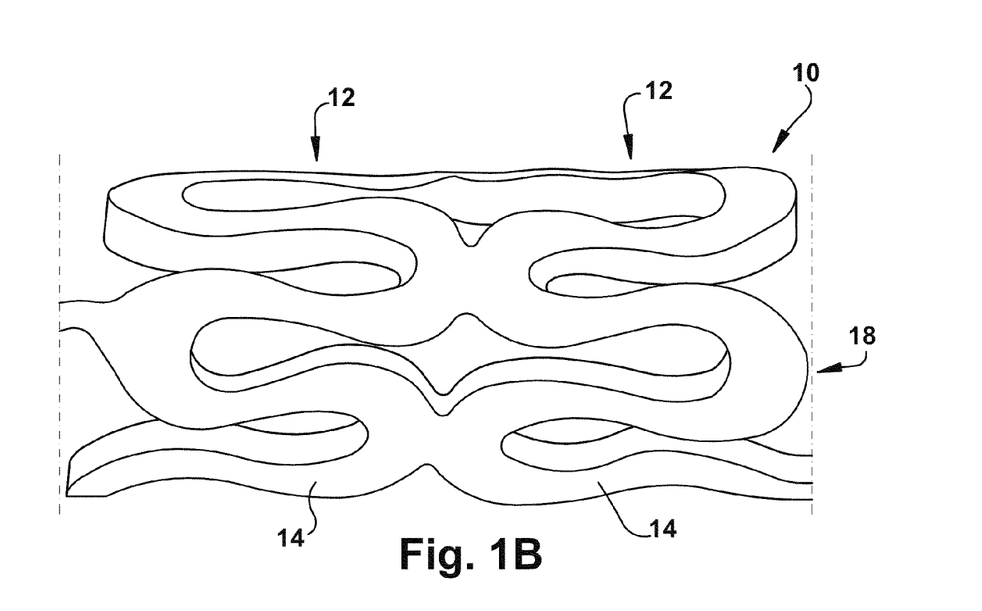
FIG. 1B is a schematic illustration showing a magnified portion of the vascular implant (FIG. 1A) in a collapsed configuration.

The present invention relates generally to an implantable vascular device for interventional therapeutic treatment or vascular surgery, and more particularly to a bioresorbable polymeric scaffold or stent that exhibits a homogeneous stress distribution in both collapsed and expanded configurations. As representative of one aspect of the present invention, FIGS. 1A-B illustrate a bioresorbable vascular implant 10 comprising one or more annular support members 12 for implantation into a bodily lumen. The one or more annular support members 12 comprise a plurality of struts 14, each of which includes a mid-section 16 and a hinge region 18. Unlike balloon-expandable vascular implants of the prior art (e.g., stents), which include predetermined areas of high stress (e.g., at the hinges), the vascular implant 10 of the present invention exhibits improved radial resistance in an expanded configuration and under dynamic load conditions (e.g., when expanded in a bodily lumen, during crimping, or in a pulsating bodily lumen). The radial resistance is improved by diffusing and limiting the maximum occurring stresses to avoid creep due to high frequency radial load. As a consequence, deformation is more evenly distributed or absorbed from the mid-section 16 of the struts 14 to the highest moment area.

I. Bioresorbable Vascular Implants

One aspect of the present invention includes a bioresorbable vascular implant 10 comprising one or more annular support members 12. The vascular implant 10 can comprise any member, device, or apparatus having a substantially tubular framework and being capable of implantation into a bodily lumen. As described in more detail below, the vascular implant 10 is comprised of at least one viscoelastic material that enables transition of the vascular implant between a collapsed configuration and an expanded configuration.

In one example of the present invention, the vascular implant 10 can comprise a scaffold. Non-limiting examples of scaffolds can include support members, collapsible members, expandable members, distensible members, solid structures, mesh structures, braided devices, porous structures, struts, membranes, bladders, umbrella-type devices, ribs, spokes, frames, and combinations thereof. Scaffolds may be fully covered, partially covered, or uncovered. Covered scaffolds may comprise skeletons that are partially or fully covered by membranes, fabrics, films, multiple layers, and/or coated.

In another example of the present invention, the scaffold can comprise a stent.

As shown in FIG. 1, the vascular implant 10 comprises one or more annular support members 12. Where the vascular implant 10 comprises two annular support members 12, at least one cross-strut 20 can intersect the annular support members. The at least one cross-strut 20 can be made of the same or different viscoelastic material as the one or more annular support members 12. The at least one cross-strut 20 can have a degradation or resorption rate that is slower, faster, or the same as the degradation or resorption rate of the one or more annular support members 12. For example, the at least one cross-strut 20 can have a degradation or resorption rate of about 90 or more days, about 60 days, or about 30 or fewer days.

The vascular implant 10 can include any number of cross-struts 20. To provide the vascular implant 10 with better flexibility when implanted in tortuous vasculature, for example, it may be desirable to include fewer cross-struts 20 so that the vascular implant can adapt to the shape of the vasculature upon degradation (e.g., dismantling or breaking) or resorption of the cross-struts in a shorter period of time. It will be appreciated that the inclusion or omission of cross-struts 20 as part of the vascular implant 10 will depend upon the particular application for which the vascular implant is intended, and that the period of time for degradation or resorption will depend upon the material grade used to form the cross-struts, the cross-sectional shape of the cross-struts, the anatomy of the vasculature, and the number of cross-struts. Additionally, it will be appreciated that the cross-struts 20 can have any suitable size and shape other than the rod-shaped configuration shown in FIGS. 2A-C.

Each of the one or more annular support members 12 includes a first end 22, a second end 24, and a channel 26 (FIG. 1A) extending between the ends. As noted above, each of the one or more annular support members 12 (FIGS. 2A-C) also comprises a plurality of struts 14 interconnected by a hinge region 18. Each of the plurality of struts 14 and the hinge region 18 define a cross-section. The cross-section of each of the struts 14 and the hinge region 18 can be rectangular, circular, ovoid, square, or any other desired shape.

Figures 2A, 2B, 2C, 2D, 2E:
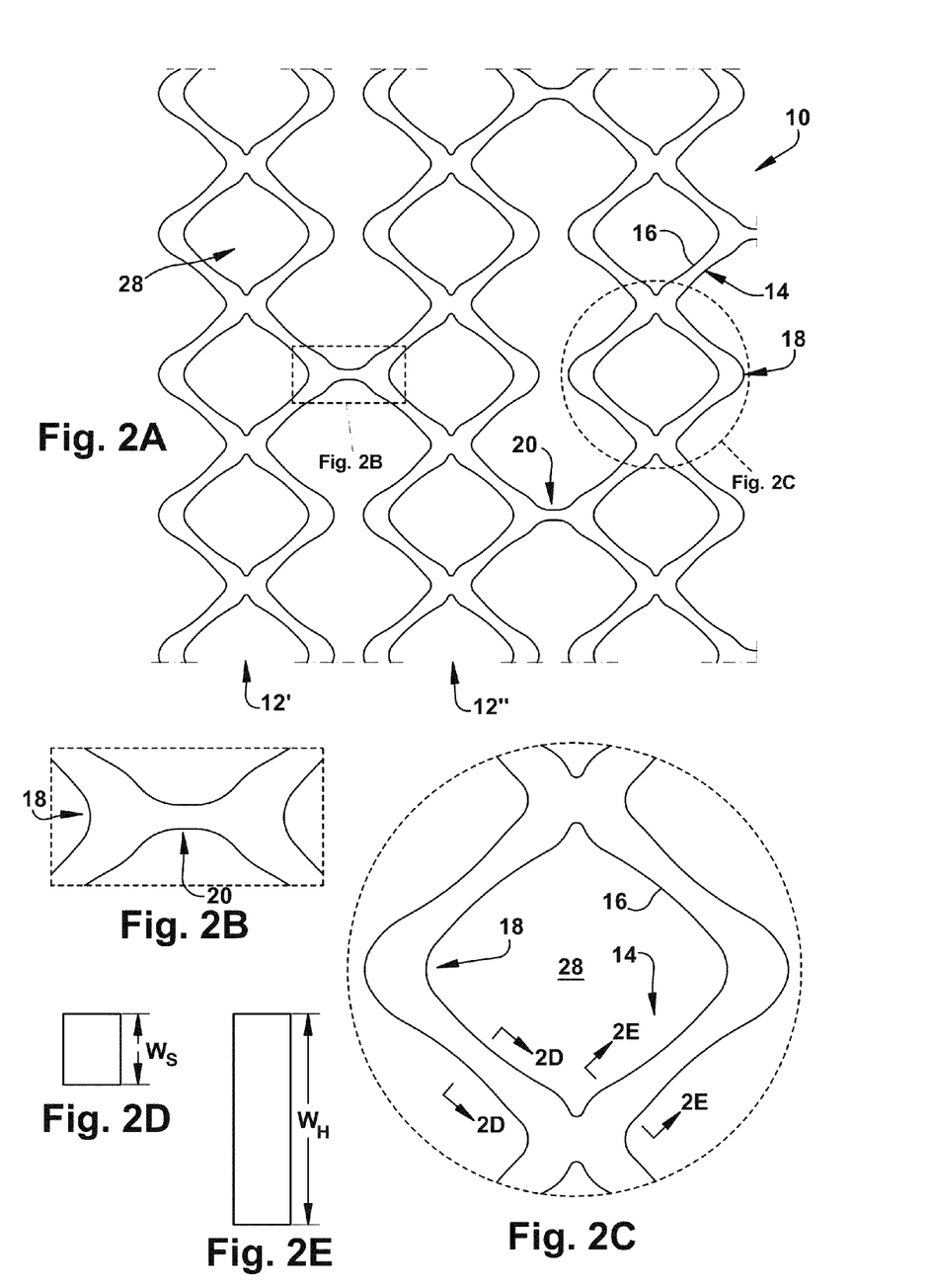
FIG. 2A is a schematic illustration showing a portion of the vascular implant in FIG. 1A.
FIG. 2B is a schematic illustration showing a magnified portion (dashed rectangle) of the vascular implant in FIG. 2A.
FIG. 2C is a schematic illustration showing a magnified portion (dashed circle) of the vascular implant in FIG. 2A.
FIG. 2D is a cross-sectional view taken along Line 2D-2D in FIG. 2C.
FIG. 2E is a cross-sectional view taken along Line 2E-2E in FIG. 2C.

In one example of the present invention, each of the struts 14 (FIGS. 2A-E) includes a mid-section 16 that defines a width $W_S$, and each of the hinge regions 18 defines a width $W_H$. As shown in FIG. 2A, a first annular support member 12' comprises a series of repeating V-shaped struts 14 connected by hinge regions 18, and a second annular support member 12" comprises a series of repeating V-shaped struts also connected by hinge regions. It will be appreciated that each of the struts 14 comprising the annular support member(s) 12 can have an identical or different configuration (e.g., shape and size), depending upon the intended application of the vascular implant 10.

Each of the annular support members 12 includes a plurality of cells 28 defined by the struts 14 and the hinge regions 18. The cells 28 allow crimping of the vascular implant 10 from a larger diameter (i.e., the expanded configuration) to a smaller diameter (i.e., the collapsed configuration) without substantially altering the construction of the cross-struts 20 or the annular support members 12. Such cells 28 may be formed by standard processing techniques, such as molding, laser cutting, engraving, or photolithography. Each annular support member 12 can include a desired number of cells 28. For example, each annular support member 12 can include about 4 to about 15 cells 28, and may preferably be about 5 to about 6 cells.

Figure 3A:
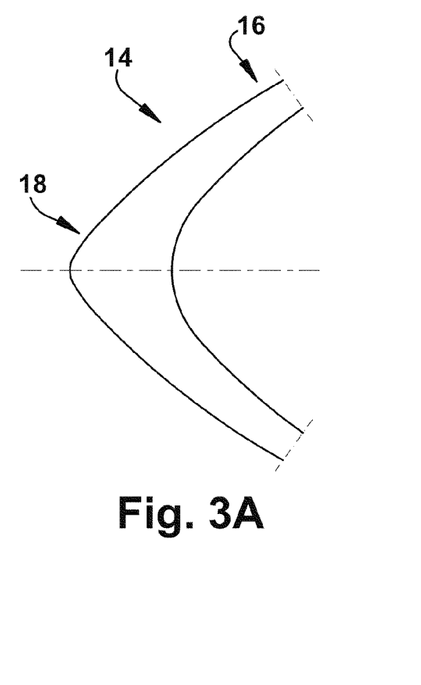
FIG. 3A is a schematic illustration showing a magnified side view of a hinge region of the vascular implant in FIG. 1A.
Figure 3B:
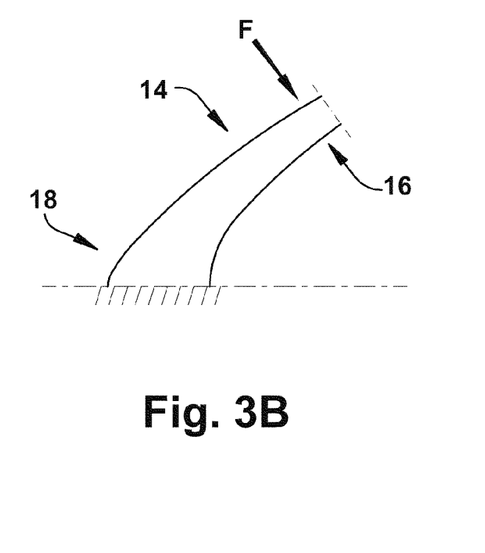
FIG. 3B is a schematic illustration showing a load (arrow) being applied to a portion of the hinge region in FIG. 3A.
Figure 3C:
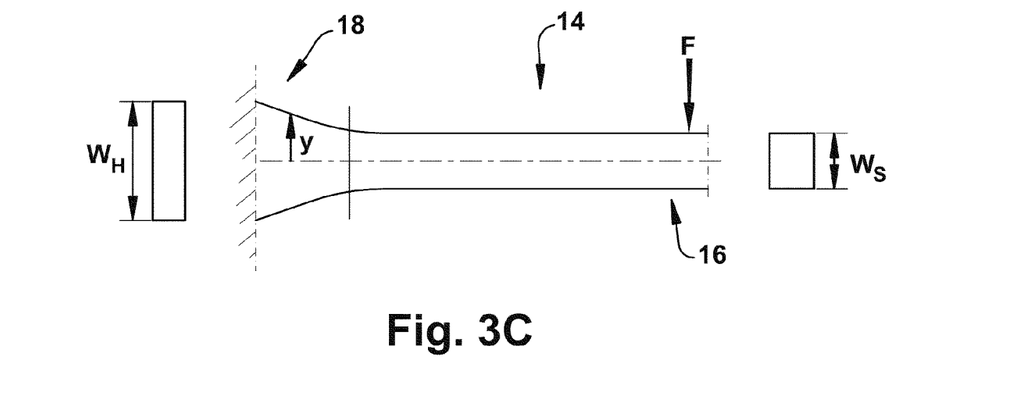
FIG. 3C is a schematic illustration showing a free body diagram of the hinge region in FIG. 3B.
Figures 4A, 4B, 4C:
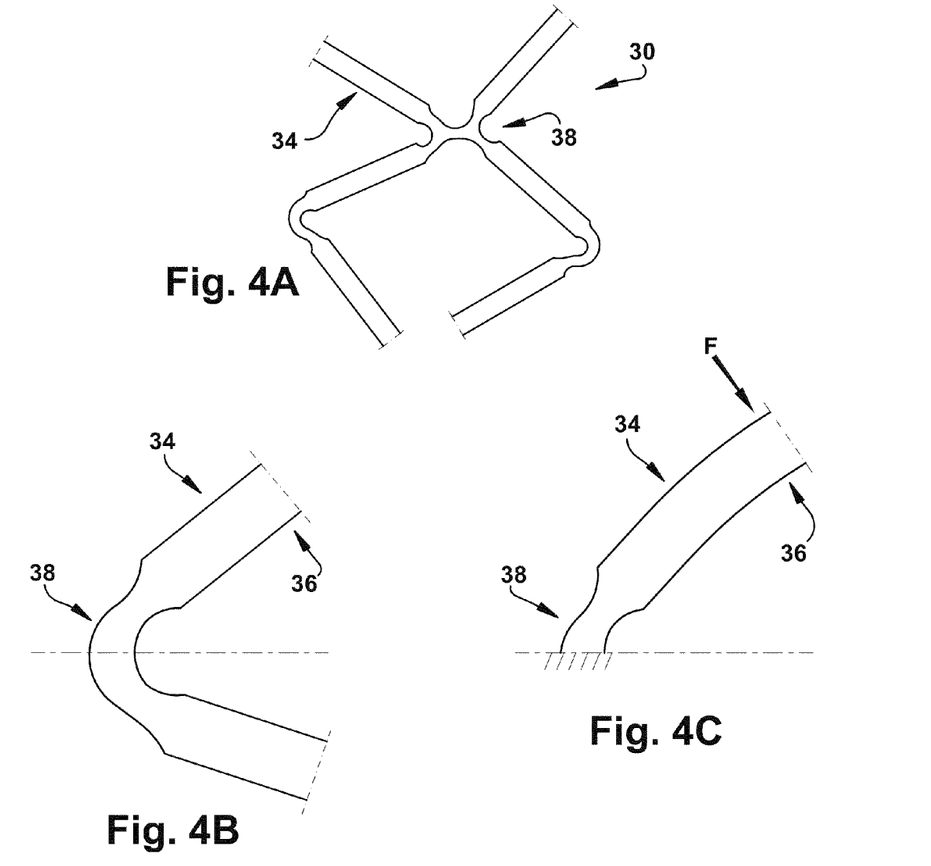
FIG. 4A is a schematic illustration showing a conventional scaffold having tapered hinge regions.
FIG. 4B is a schematic illustration showing a magnified side view of a hinge region of the scaffold in FIG. 4A.
FIG. 4C is a schematic illustration showing a load (arrow) being applied to a portion of the hinge region in FIG. 4B.
Figure 4D:
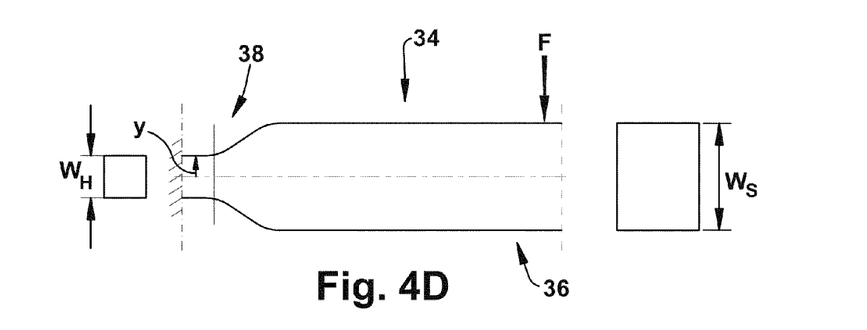
FIG. 4D is a schematic illustration showing a free body diagram of the hinge region in FIG. 4C.
Figure 5A:
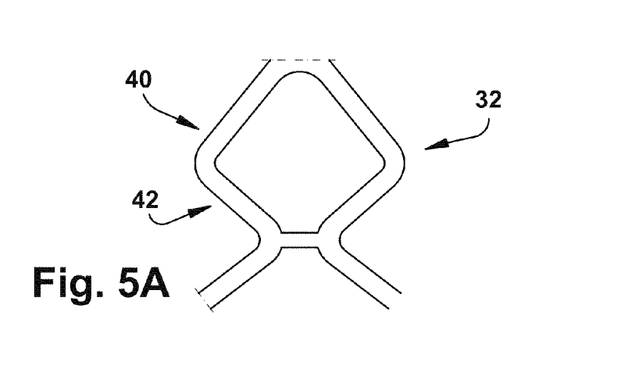
FIG. 5A is a schematic illustration showing another conventional scaffold having hinge regions and strut mid-sections with equally-sized cross-sections.
Figure 5B:
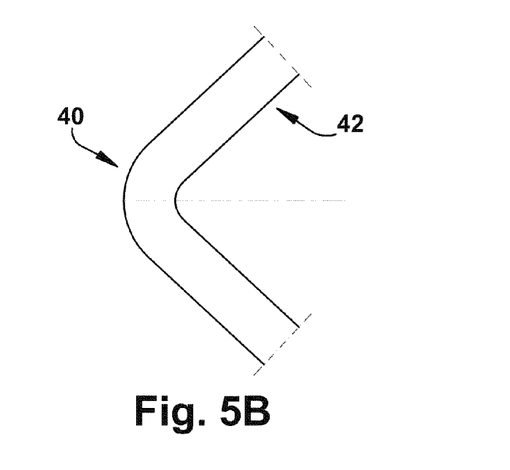
FIG. 5B is a schematic illustration showing a magnified side view of a hinge region of the scaffold in FIG. 5A.
Figure 5C:
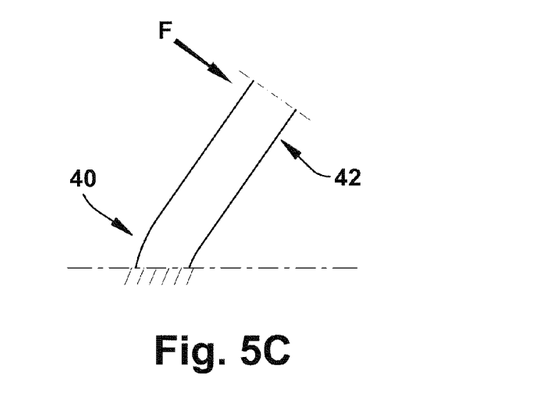
FIG. 5C is a schematic illustration showing a load (arrow) being applied to a portion of the hinge region in FIG. 5B.
Figure 5D:
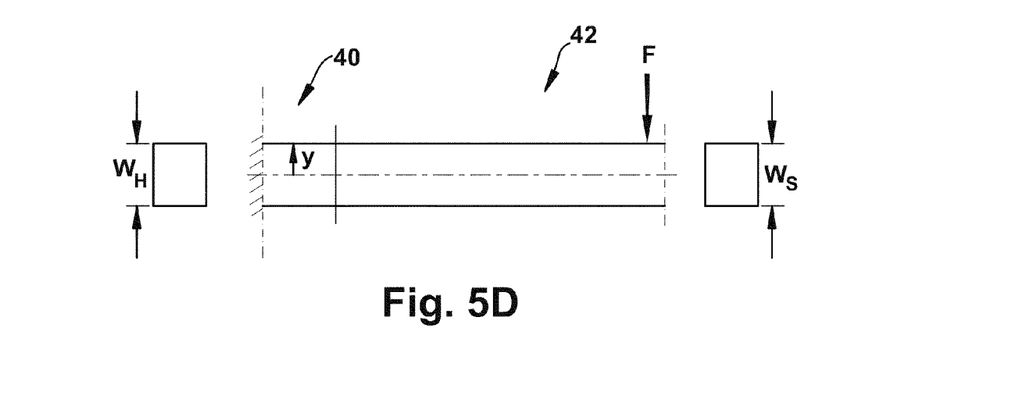
FIG. 5D is a schematic illustration showing a free body diagram of the hinge region in FIG. 5C.
Figure 6:
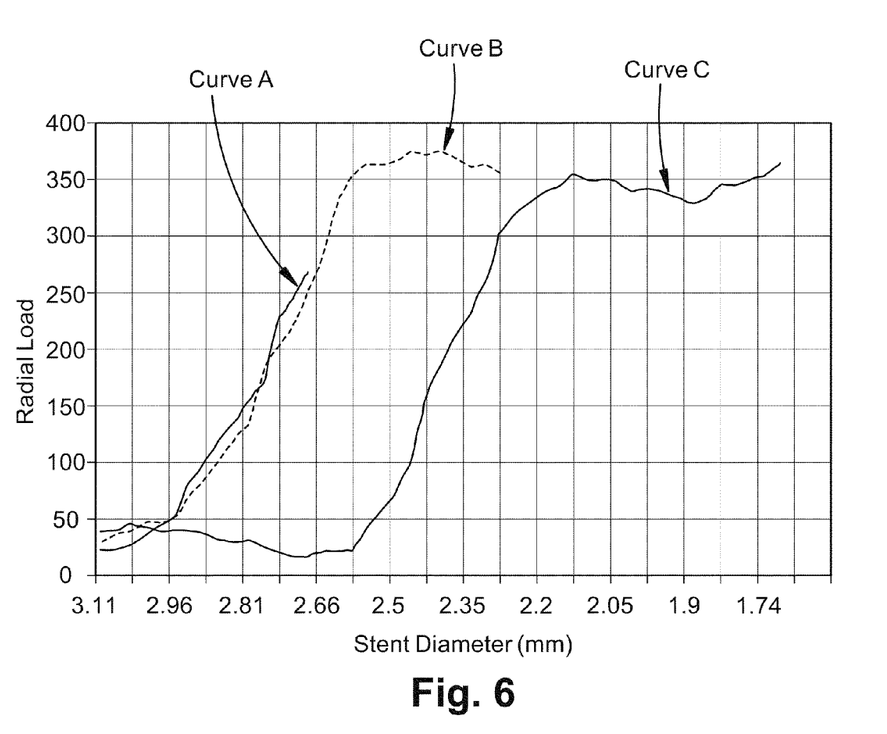

The present invention can best be understood by referring to FIGS. 3A-C. As seen in FIGS. 3A-C, the width $W_S$ of at least a part of each of the struts 14 is less than the width $W_H$ of each of the hinge regions 18. For example, the width $W_S$ at the mid-section 16 can be about 150 μm or greater, and the width $W_H$ of the hinge region 18 can be about 250 μm or greater. In one example of the present invention, the width $W_S$ at the mid-section 16 can be about 160 μm, and the width $W_H$ at the hinge region 18 can be about 300 μm.

The width $W_H$ can taper substantially continuously from the hinge region 18 to the mid-section 16 of each of the struts 14. The effect of this tapering is to cause an increase in the moment of inertia from the mid-section 16 towards the hinge region 18 to resist a radial load or its tangentially derived component applied to the vascular implant 10 (i.e., in the expanded configuration). In other words, the effect will be a greater resistance to deformation at the hinge regions 18 (i.e., where the bending moments are high), and to make the overall stress deformation more uniform. Consequently, the homogenous distribution of stresses throughout the one or more annular support members 12 ensures that the tangentially derived radial strength and mechanical resistance of the vascular implant 10 are not compromised when the vascular implant is being expanded and then subject to a radial load.

The ideal reduction in width is a complex function, driven by efforts to keep the bending radius constant. For example, bending of a rectangular beam is controlled by the formula:

$$1/R = 12FL/(ETW^3);$$

where R is the radius of curvature of the hinge region 18, F is the applied force, L the distance from the endpoint, E is Young's modulus, T is the thickness of the strut 14, and W the strut width. Thus, as a guideline, the strut width W should vary as the cube root of the distance from one of the ends of the strut 14. That is, at any point along the mid-section 16 of the strut 14, the width W should be proportional to the cube root of the distance from one of the ends that point is closest to. However, any taper, even a simple linear tapered reduction in width W would still represent a significant improvement over a constant width strut. Because the struts 14 are wider at their hinge regions 18, the overall vascular implant 10 can handle greater compressive and expanding forces. Therefore, the vascular implant 10 can handle greater fatigue stresses, which can result in a longer lasting and stronger vascular implant.

In trying to minimize the maximum stress experienced by the hinge regions 18, the present invention utilizes a structural geometry that distributes stress to areas of the struts 14 (e.g., the mid-section 16) that are less susceptible to failure than others. For example, one of the most vulnerable areas of conventional stent structures is the radius of the on the inside of the hinges as the stent is expanding. These then inside radii of the hinges are normally the area with the highest level of stress on such stent structures.

FIGS. 4A-D and FIGS. 5A-D illustrate examples of conventional stent structures 30 and 32, respectively. As shown in FIGS. 4A-D, certain conventional stent structures 30 include tapered hinges 34 having a width $W_H$ that is less than the width $W_S$ of the mid-section 36 of the strut 38. Such a stent configuration is disadvantageous as the moment of inertia would increase from the hinge 34 to the mid-section 36 upon application of a radial load and, thus, increase stresses at the hinge. Similarly, as shown in FIGS. 5A-D, other conventional stent structures 32 include hinges 40 and strut mid-sections 42 having widths $W_H$ and $W_S$ that are equal. Such a stent configuration is disadvantageous as the moment of inertia would remain constant from the hinge 40 to the mid-section 42 upon application of a radial load, thus yielding a non-homogenous stress distribution throughout the stent structure 32.

Other examples of conventional stent structures are disclosed in U.S. Pat. No. 6,190,406 to Duerig et al., U.S. Pat. No. 7,753,948 to Roeder et al. (hereinafter, "Roeder I"), and U.S. patent application Ser. No. 11/454,303 to Roeder et al. (hereinafter, "Roeder II"). Duerig teaches self-expandable stents that exhibit evenly distributed strains and are made of superelastic materials, such as Nitinol. Roeder I teaches self-expandable stents with evenly distributed stresses, which can be moved into a collapsed configuration and placed into a sheath, which is required to maintain the stent in a collapsed state for intravascular delivery. Roeder I also teaches that the stents are made from elastic, non-elastic, and superelastic materials (e.g., Nitinol), but fails to teach that the stents are made of viscoelastic polymers. Roeder II teaches self-expandable stents that can accommodate large amounts of strain, without permanent damage, in a collapsed state. Roeder II also teaches that the stents are made from elastic, non-elastic, and superelastic materials (e.g., Nitinol), but fails to teach that the stents are made of viscoelastic polymers.

As noted above, one of the advantages of the present invention is that stress is distributed more evenly throughout the vascular implant 10 upon application of a radial load. In particular, stress levels may be redistributed away from the hinge regions 18 and distributed along the length of the struts 14, such as at or near the mid-section 16 of each of the struts. As a result, the maximum stress levels at the hinge regions 18 may be reduced.

Another advantage of the present invention is that by homogenously distributing stresses throughout the vascular implant 10, the fatigue life of the vascular implant may be increased. Fatigue life may be a concern with traditional stent structures since the stents remain slightly compressed by the artery wall or other tissue structure even after implantation. This compression introduces an operational stress into the stent structure. Because a subject's heart typically causes the arteries in the vascular system to expand and contract with each heartbeat, an implanted stent normally expands and contracts a small amount each time the heart beats. In conventional stent structures, this may cause fatigue failure in the hinges of the stent structure since the cycles of operational stress are concentrated in the hinges. By contrast, the vascular implant 10 of the present invention may reduce the risk of failure at the bends or hinges by minimizing the operational stress levels.

All or only a portion of the vascular implant 10 can be formed from at least one viscoelastic material. Viscoelastic materials of the present invention can include any one or combination of materials that exhibit both viscous and/or elastic characteristics when undergoing deformation. A viscous behavior is characterized by linear variation of shear flow and strain with time when a stress is applied, and by absence of memory of the initial state. An elastic material strains instantaneously when stretched and just as quickly return to its original state once the stress is removed. A viscoelastic material can exhibit viscous and/or elastic behaviors depending on temperature and rate of deformation. In the case of viscoelastic polymers, elasticity is usually the result of bond stretching along crystallographic planes in an ordered solid or the lack of time for macromolecular structures to deform (i.e., below the glass transition temperature or at high rate, speed of deformation), whereas viscosity is the result of movements of parts of macromolecules and/or of macromolecules and/or of macromolecular framework (above the glass transition temperature or at low rate, speed of deformation). In the case of implantable polymeric devices, the stress-strain behavior depends on the position of the glass transition with respect to body temperature. The viscoelastic material or materials used to form the vascular implant 10 of the present invention have elements of both of these properties and, as such, exhibit time-dependent strain.

In one example of the present invention, the vascular implant 10 can be formed from one or a combination of viscoelastic materials, such as degradable and bioresorbable polymers (e.g., thermoplastic polymers). The vascular implant 10 can be formed from a degradable and bioresorbable polymer having a glass transition temperature (Tg) of about 32° C.<Tg<100° C. and, more particularly, about 35° C.<Tg<68° C. For instance, the vascular implant 10 may be formed from one or more degradable and bioresorbable polymers (e.g., a thermoplastic polymer or polymers) having a low working temperature range (e.g., a Tg of about 37° C.) as some materials (e.g., steel) can exhibit some viscoelasticity at high temperatures.

The polymer(s) forming the vascular implant 10 can be a homopolymer or a copolymer formed from a thin layer of one or more amorphous, bioresorbable polymers, i.e., the polymers are not crystalline at room temperature. The polymers used to form the vascular implant 10 do not generate crystalline residues upon degradation in vivo, and may or may not be cross-linked. Light cross-linking may be used, for example, if thermal and viscoelastic characteristics that allow education, crimping, and deployment of the vascular implant 10 are sufficiently maintained.

Examples of polymers that may be used to form the vascular implant 10 can include, but are not limited to, polylactic acid, polyglycolic acid, polycaprolactone and their associated copolymers, polycarbonates, polyorthoesters, polyanhydride, polydioxanone and polyhydroxybutyrate, polyamides, polyurethanes, polyureas, polyethers, polysaccharides, polyamines, polyphosphates, polyphosphonates, polysulfonates, polysulfonamides, polyphosphazenes, polynorbornene and copolymers of polynorbornene, blends of polybornene with KRATON® (thermoplastic elastomer) and polyethylene, styrenic block copolymer elastomers (e.g., styrene-butadiene), polymethylmethacrylate (PMMA), polyethylene, polyisoprene, polycaprolactone and copolymers of polycaprolactone, copolymers of polylactic acid, copolymers of polyglycolic acid, polyenes, nylons, polycyclooctene (PCO), polyvinyl acetate (PVAc), polyvinylidene fluoride (PVDF), blends of polyvinyl acetate/polyvinylidine fluoride (PVAc/PVDF), blends of polymethylmethacrylate/polyvinyl acetate/polyvinylidine fluoride (PVAc/PVDF/PMMA), polyvinylchloride (PVC), blends, derivatives, copolymers, and/or combinations thereof.

In one example of the present invention, the vascular implant 10 can be formed from lactic acid-based stereocopolymers (PLAx copolymers composed of L and D units, where X is the percentage of L-lactyl units) (55<Tg<60), copolymers of lactic and glycolic acids (PLAxGAy, where X is the percentage of L-lactyl units, Y is the percentage of glycolyl units, and the Tg of the copolymer is above about 45° C.), and poly(lactic-co-glycolic-co-gluconic acid), where the OH groups of the gluconyl units can be more or less substituted (pLAxGayGLz, where X is the percentage of L-lactyl units, Y is the percentage of glycolyl units, and Z is the percentage of gluconyl units such that the Tg of the terpolymer is above about 45° C.).

In another example of the present invention, the vascular implant 10 can be formed from a polylactic acid stereocopolymer produced from L and DL lactides. The polymer is designated herein as "PLAX", where X represents the percentage of the L-lactic acid units in the mixture of monomers used to prepare the lactides. X can be in the range of about 2 to about 98 and, for example, about 20 to about 80.

In yet another example of the present invention, the vascular implant 10 can be formed from comprise a polylactic acid and glycolic acid copolymer produced from L and DL lactides and glycolides. The polymer is designated herein as "PLAXGAY", where Y represents the percentage of glycolic acid units in the mixture of monomers used to prepare the copolymers. The copolymers do not contain glycolyl repeating units since such units are known to be more inflammatory than lactyl repeating units. The polymers can be prepared using Zn metal or Zn lactate as an initiator. To ensure good initial mechanical properties of the vascular implant 10, the molecular weight of the copolymer can be above about 20,000 daltons and, for example, about 100,000 daltons or larger. The polydispersity, I=Mw/Mn, can be below about 2 and should not greatly reflect the presence of low molecular weight oligomers smaller than about 2,000 daltons (as determined, for example, by size exclusion chromatography).

II. Educating and Crimping of the Bioresorbable Vascular Implant

The vascular implant 10 can be formed by standard techniques, such as extrusion, molding, spinning, injection molding, laser cutting, combinations thereof, or any other processing technique that transforms the viscoelastic polymer(s) into a hollow device having a tubular framework. The vascular implant 10 formed by any one or combination of these processes can be configured to have a final predetermined configuration (e.g., shape, length, thickness, diameter) that is tailored to the application for which the vascular implant is to be utilized. For example, the vascular implant 10 may be pre-formed to an initial diameter and then heated to a temperature at or above the selected glass transition temperature. The vascular implant 10 may then be crimped (e.g., using either mechanical means and/or cooling) to a smaller, contracted profile suitable for delivery into a bodily lumen. The vascular implant 10 can then be cooled and, prior to implantation, assembled onto a guide catheter (not shown) or other delivery system (e.g., a balloon). A more detailed discussion of processes that can be used to form the vascular implant 10 is disclosed in PCT Publication No. WO 2005/096992 A1, the entirety of which is hereby incorporated by reference.

The vascular implant 10 can be formulated to carry and deliver a variety of materials or therapeutic agents, provided that these materials or agents do not form a solid solution with the viscoelastic polymer(s) and do not act as a plasticizer that significantly alters implant functionality. The materials or agents can be deposited on the exterior or interior surface of the vascular implant 10 either by impacting or chemical coupling. Such materials or agents can include pharmaceuticals, pharmaceutically active agents, drugs, genetic agents, non-genetic agents, and cells. A wide variety of therapeutic agents can be employed in conjunction with the present invention, including those used for the treatment of a wide variety of diseases and conditions (i.e., the prevention of a disease or condition, the reduction or elimination of symptoms associated with a disease or condition, or the substantial or complete elimination of a disease or condition), such as cardiovascular diseases and cancer.

III. Procedures for Determining Times and Temperatures for Educating and Crimping of the Bioresorbable Vascular Implant Temperatures and times suitable for educating the vascular implant 10 and thereby developing a vascular implant that is resistant to negative recoil can be assessed by first crimping the vascular implant onto a balloon catheter. The balloon is then inflated to initiate expansion of the vascular implant 10. The balloon is removed and the vascular implant 10 is stored at about 37° C. While in storage, the vascular implant 10 may increase in diameter because of the positive recoil properties of the vascular implant. If the vascular implant 10 exhibits little to no negative recoil when stored under these conditions for a period of about 4 to 6 weeks (e.g., the time estimated for an artery wall to recover from PTC angioplasty), the times and temperatures employed for educating the vascular implant 10 are appropriate. In those cases where the vascular implant 10 exhibits a small amount of recoil, the vascular implant can be educated at a diameter slightly larger than the final predetermined diameter to compensate for the small amount of negative recoil.

Temperatures and times for crimping the vascular implant 10 to a reduced diameter can be assessed by allowing the vascular implant-mounted balloon catheter to stay at about room temperature or at the storage temperature. If the crimped vascular implant 10 stays collapsed at the small diameter corresponding to the deflated balloon under these conditions, the times and temperatures employed during crimping are appropriate. Optimization of the imparted mechanical properties of the vascular implant 10 (e.g., positive recoil) can be achieved by storing the finished product at a room temperature below about 20° C. For example, the finished product can be refrigerated at about 6° C. to about 8° C.

IV. Deployment of the Bioresorbable Vascular Implant

After forming the vascular implant 10, the vascular implant can be implanted in a bodily lumen to treat any one or combination of diseases or conditions (e.g., stenosis or a vulnerable plaque). Examples of bodily lumens or passageways into which the vascular implant 10 can be implanted include the gastrointestinal tract (e.g., bile ducts, colon, duodenum), esophagus, trachea, bronchi, urinary tract (e.g., urethra, prostate, ureters), pancreatic duct systems, the gut, eye ducts, spermatic and fallopian tubes, and vasculature, such as arteries and veins (e.g., femeroiliac arteries, the carotid artery, vertebro-basilar arteries, renal arteries, coronary blood vessels, peripheral blood vessels, intracranial blood vessels, etc.).

The vascular implant 10 can be deployed by a variety of processes. For example, the vascular implant 10 can be introduced into the bodily lumen or passageway using a guide catheter, for example, and then advanced to a target site within the bodily lumen (e.g., the site of stenosis or a vulnerable plaque). The diameter and placement of the vascular implant 10 can be determined by any method. For example, part or all of the vascular implant 10 can be coated or wrapped with a radiopaque material to allow real-time visualization of the vascular implant during implantation. One example of such a radiopaque material can include gold, which is non-irritating, substantially non-allergic, offers high fluoroscopic visibility in a very thin layer, and is believed to decrease thrombus formation.

In one example of the present invention, the vascular implant 10 can include at least two markers (not shown) disposed on that the diameter of the vascular implant may be determined in real-time. The markers can be applied to the vascular implant 10 in any number of ways, such as a ribbon that is crimped onto a strut of the vascular implant and/or a partially sputtered heavy metal coating. As described further below, the markers can help to determine if the vascular implant 10 has been properly expanded, and if the diameter of the vascular implant has increased or decreased at any given time.

Imaging modalities used to detect the markers are known in the art and can include X-ray, magnetic resonance imaging (MRI), and ultrasound imaging. The markers may be used to track the location of the vascular implant 10 as it travels through the subject's body, which greatly assists in determining whether the vascular implant is traveling the correct path through the subject. Further, this assists in placing the vascular implant 10 at the correct site within the bodily lumen.

It will be appreciated that the vascular implant 10 can alternatively include at least three markers. The use of at least three markers enables the three-dimensional location of the vascular implant 10 to be determined at any time during implantation. This feature ensures that the vascular implant 10 does not have rotational motion within the bodily lumen, which may occur if the outer diameter of the vascular diameter is less than the inner diameter of the bodily lumen in which the vascular implant is placed. Rotational motion of the vascular implant 10 within the bodily lumen is disfavored because it can increases blood flow turbidity and thus thrombogenesis. In the event that rotational motion is detected during implantation of the vascular implant 10, it will be understood that the diameter of the vascular implant should then be appropriately increased.

After the vascular implant 10 is positioned at the target site within the bodily lumen, the vascular implant may be expanded into its final predetermined shape. The vascular implant 10 can be expanded using any one or combination of known techniques, such as via a balloon, inflation fluid, and/or the bodily heat of the subject. For example, the vascular implant 10 can be expanded using a combination of sustained balloon expansion and memory recovery (i.e., as the select Tg of the stent is reached) as disclosed in U.S. patent application Ser. No. 12/282,738, which is hereby incorporated by reference in its entirety.

The slow and sustained, memory-based positive recoil of the vascular implant 10 prevents or mitigates uncontrolled and excessive expansion of the vascular implant, which can cause damage to the tissue at the target site. Additionally, since the viscoelastic material(s) of the vascular implant 10 exhibit time-dependent strain, slow and sustained deployment of the vascular implant avoids the cracks and crazing typically associated with deployment of polymeric scaffolds or stents. During and after expansion, the stresses that are homogenously distributed throughout the vascular implant 10 ensure that the radial strength and mechanical resistance of the implant are not compromised, thereby preventing or mitigating undesirable or deleterious effects to the stent (i.e., stent collapse or recoil). Consequently, the deployed vascular implant 10 not only exhibits increased radial rigidity to sustain elastic arterial recoil, but also avoids crush by mitigating or preventing stresses above the yield stress.

The following example is for the purpose of illustration only and is not intended to limit the scope of the claims, which are appended hereto.

Example

The coronary vasculature of 32 pigs, 16 house swine, and 16 mini-pigs were implanted with 2 bioresorbable stents (as are schematically illustrated in FIGS. 1A-2E) per pig. All of the stents were delivered to their respective target sites and properly deployed following appropriate instruction. The house swine were sacrificed at 28 days and the mini-pigs at 90 days.

Figure 7A:
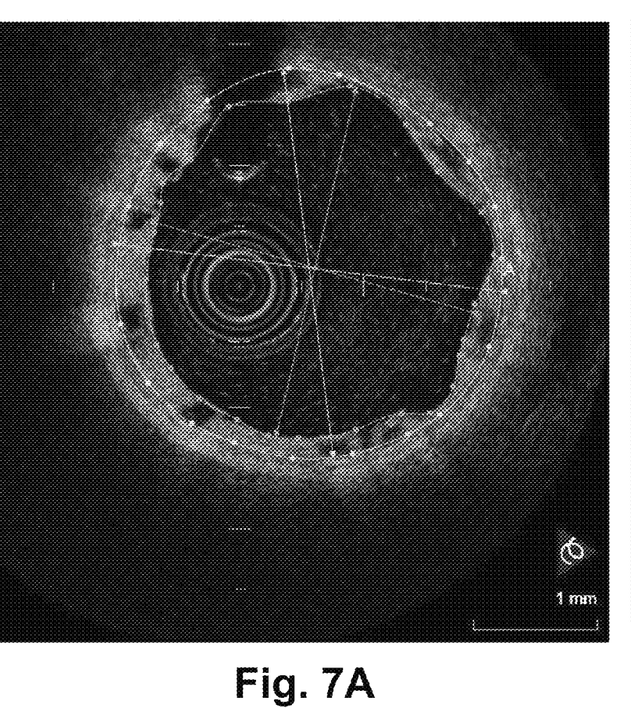
FIGS. 7A-B are a series of OCT images showing a bioresorbable vascular implant of the present invention perfectly opposed to an artery wall and providing clear radial support thereto.
Figure 7B:
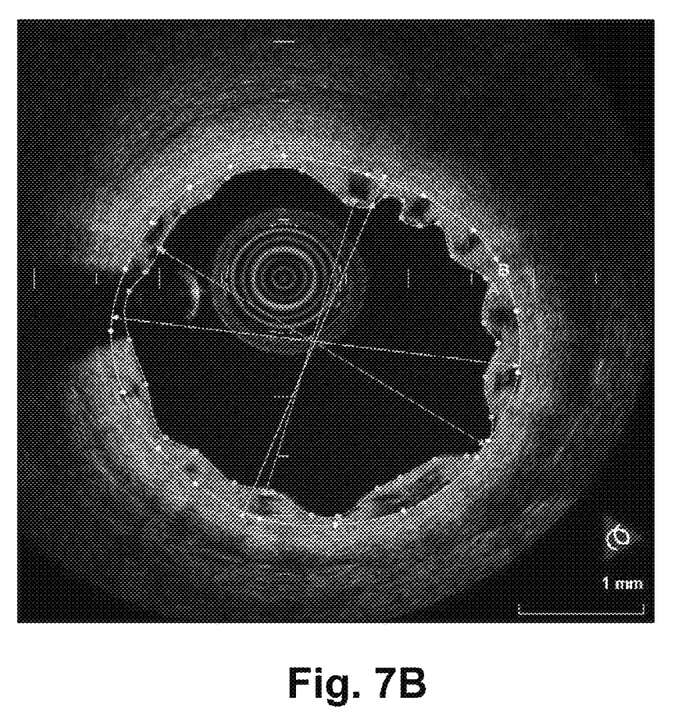

One month following stent implantation, the percentage of restenosis was less than 50%, with a measured average late lumen loss of around 0.6 mm. As can be appreciated in FIGS. 7A-B, the stents were perfectly opposed to the artery wall at 30 days and at 90 days, thereby proving clear radial support.

Figure 8:
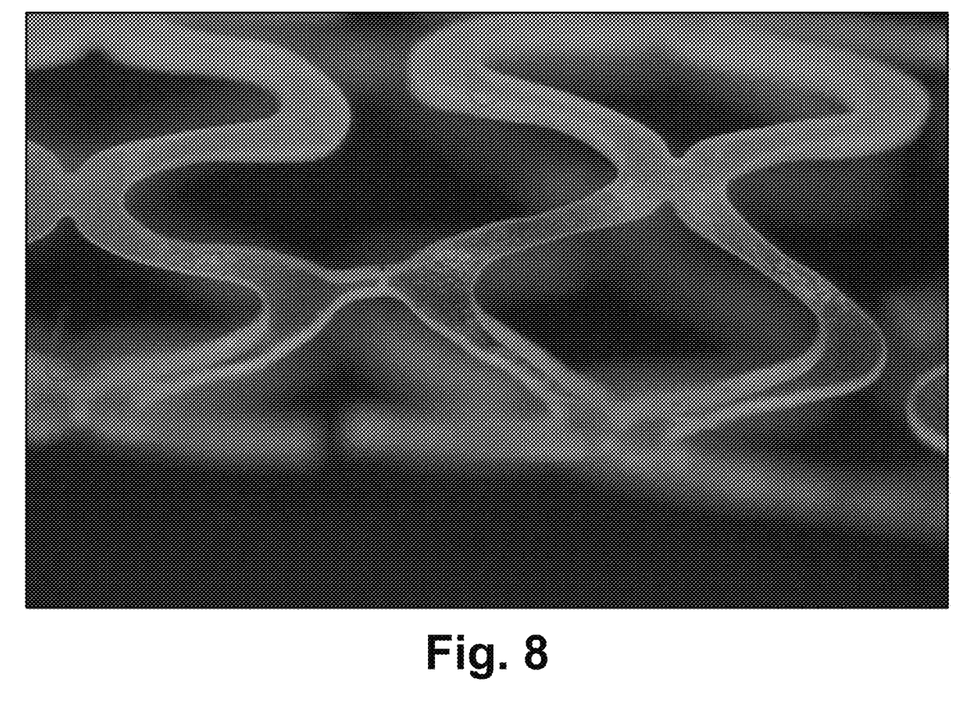
FIG. 8 is a magnified photograph showing breakage of a cross-strut of the bioresorbable vascular implant in FIGS. 7A-B following implantation in swine vasculature for 30 days.
Figure 9A:
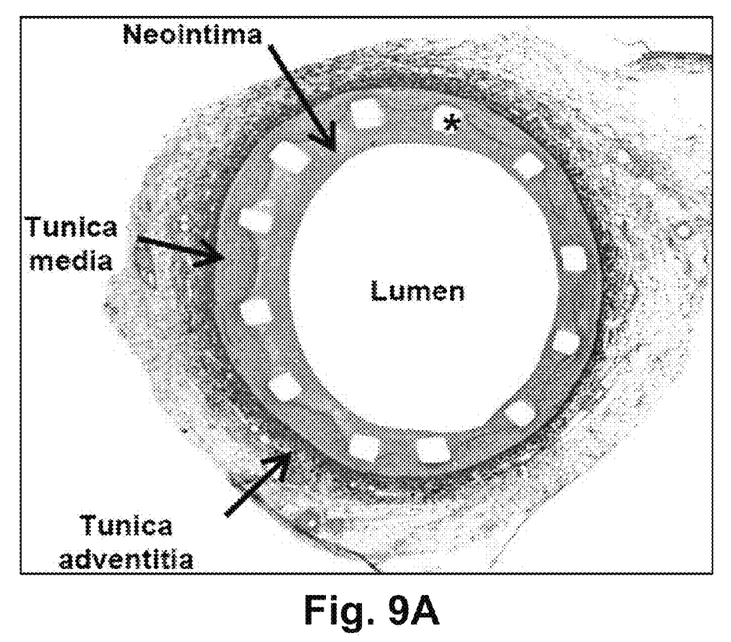
FIGS. 9A-B are a series of pathology slides showing good biocompatibility of the bioresorbable vascular implant in FIGS. 7A-B following implantation in swine vasculature for 30 days.
Figure 9B:
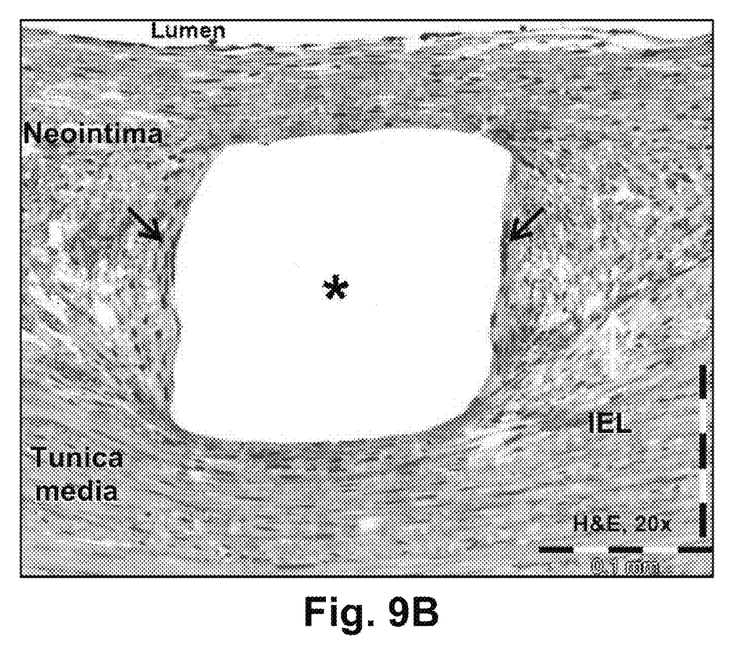

Furthermore, some stents were explanted and processed through an enzymatic digestion protocol. Residual radial force was measured on the recovered stents. As shown in FIG. 8, link breakage was demonstrated in one of the recovered stents. The radial strength and stiffness at 30 days was not inferior as compared to values prior to implantation. Additionally, histology analysis demonstrated good biocompatibility of the stents at 30 days (FIGS. 9A-B). Histology was performed by CBSET, 500 Patriot Way, Lexington, Mass. 02421, USA.

From the above description of the invention, those skilled in the art will perceive improvements, changes, and modifications. Such improvements, changes, and modifications are within the skill of the art and are intended to be covered by the appended claims.

Having described the invention, the following is claimed:

1. A bioresorbable vascular implant having a tubular framework and being for implantation in a bodily lumen, said vascular implant comprising:
   one or more annular support members, each of said one or more annular support members including a plurality of struts interconnected by a hinge region having a width, each of said plurality of struts including a mid-section having a width;
   wherein said vascular implant is comprised of at least one viscoelastic material that enables transition of said vascular implant between a collapsed configuration and an expanded configuration, each of said plurality of struts and said hinge region defining a cross-section;
   wherein the moment of inertia increases from each said mid-section towards each said hinge region to accommodate said transition and resist a radial load applied to said vascular implant in the expanded configuration;
   wherein the width of each of said plurality of struts tapers substantially continuously from each said hinge region to each said mid-section; and
   wherein stresses between said mid-section of said plurality of struts and said hinge region are evenly distributed under application of the radial load to said vascular implant in the expanded configuration.

2. The bioresorbable vascular implant of claim 1, wherein said vascular implant is a scaffold.

3. The bioresorbable vascular implant of claim 1, wherein said vascular implant is a stent.

4. The bioresorbable vascular implant of claim 1, wherein the cross-section defines a width.

5. The bioresorbable vascular implant of claim 1 further comprising at least one cross-strut intersecting said one or more annular support members.

6. The bioresorbable vascular implant of claim 5, wherein the width of said at least one cross-strut is less than the width of said hinge region.

7. The bioresorbable vascular implant of claim 5, wherein said at least one cross-strut breaks in less than about 90 days due to degradation of the viscoelastic material comprising said at least one cross-strut following implantation of said vascular implant in the bodily lumen.

8. The bioresorbable vascular implant of claim 1, wherein said viscoelastic material comprises a thermoplastic polymer.

9. The bioresorbable vascular implant of claim 8, wherein the glass transition temperature of said thermoplastic polymer is at least about 37° C.

10. The bioresorbable vascular implant of claim 9, wherein said thermoplastic polymer is a polylactic acid (PLA) polymer.

11. The bioresorbable vascular implant of claim 10, wherein said PLA polymer is poly-DL-lactic acid.

12. The bioresorbable vascular implant of claim 1, wherein the width of each said hinge portion is about 250 µm or greater, and the width of each said mid-section is about 150 µm or greater.

13. The bioresorbable vascular implant of claim 12, wherein the width of each said hinge portion is about 300 µm, and the width of each said mid-section is about 160 µm.

14. A bioresorbable vascular implant having a tubular framework and being for implantation in a bodily lumen, said vascular implant comprising:
   one or more annular support members, each of said one or more annular support members including a plurality of struts interconnected by a hinge region having a width, each of said plurality of struts including a mid-section having a width; and
   at least one cross-strut intersecting said one or more annular support members;
   wherein said vascular implant is comprised of at least one viscoelastic material that enables transition of said vascular implant between a collapsed configuration and an expanded configuration, each of said plurality of struts and said hinge region defining a cross-section;
   wherein the moment of inertia increases from each said mid-section towards each said hinge region to accommodate said transition and resist a radial load applied to said vascular implant in the expanded configuration;

wherein the width of each of said plurality of struts tapers substantially continuously from each said hinge region to each said mid-section;

wherein stresses between said mid-section of said plurality of struts and said hinge region are evenly distributed under application of the radial load to said vascular implant in the expanded configuration; and wherein said at least one cross-strut breaks in less than about 90 days due to degradation of the viscoelastic material comprising said at least one cross-strut following implantation of said vascular implant in the bodily lumen.

15. A bioresorbable vascular implant having a tubular framework and being for implantation in a bodily lumen, said vascular implant comprising:

one or more annular support members, each of said one or more annular support members including a plurality of struts interconnected by a hinge region having a width, each of said plurality of struts including a mid-section having a width;

wherein said vascular implant is comprised of at least one viscoelastic material that enables transition of said vascular implant between a collapsed configuration and an expanded configuration, each of said plurality of struts and said hinge region defining a cross-section;

wherein the moment of inertia increases from each said mid-section towards each said hinge region to accommodate said transition and resist a radial load applied to said vascular implant in the expanded configuration;

wherein the width of each of said plurality of struts tapers substantially continuously from each said hinge region to each said mid-section;

wherein stresses between said mid-section of said plurality of struts and said hinge region are evenly distributed under application of the radial load to said vascular implant in the expanded configuration; and wherein the vascular implant is configured for use in an angioplasty procedure.

* * * * *